United States Patent [19]

Botterman et al.

[11] Patent Number: 4,498,420

[45] Date of Patent: Feb. 12, 1985

[54] CARTON FOR INSECTS

[75] Inventors: D. L. Botterman; N. A. Wolff; H. T. Ver Planck, all of Arlington, Tex.

[73] Assignee: Container Corporation of America, Chicago, Ill.

[21] Appl. No.: 572,870

[22] Filed: Jan. 23, 1984

[51] Int. Cl.³ .................... A01K 1/00; B65D 5/48
[52] U.S. Cl. ........................ 119/15; 119/17; 229/DIG. 14; 229/27; 206/527; 206/620
[58] Field of Search ........... 119/15, 17, 18, 19, 119/1; 229/15, 27, 6 H, 14; 206/527, 620

[56] References Cited

U.S. PATENT DOCUMENTS

| | | | |
|---|---|---|---|
| 1,890,951 | 12/1932 | Sherman | 229/27 |
| 2,422,438 | 6/1947 | Richards | 119/19 |
| 3,115,290 | 12/1963 | Byassee | 229/27 |
| 3,251,528 | 5/1966 | Cilluffo | 229/27 |
| 3,375,808 | 4/1968 | Freeman | 119/19 |
| 3,507,441 | 4/1970 | Wilcox et al. | 229/27 |
| 3,611,994 | 10/1971 | Bailey | 119/15 |
| 3,731,870 | 5/1973 | Buttery | 229/27 |
| 4,010,888 | 3/1977 | Gilbert | 229/52 B |
| 4,088,262 | 5/1978 | Kuehlhorn | 229/27 |

Primary Examiner—Hugh R. Chamblee
Assistant Examiner—Kris R. Schulze
Attorney, Agent, or Firm—Richard W. Carpenter

[57] ABSTRACT

A collapsible paperboard folding carton for hatching, holding, feeding and releasing insects.

2 Claims, 7 Drawing Figures

CARTON FOR INSECTS

BACKGROUND OF THE INVENTION

1. Field of the Invention

This invention relates to a carton for insects, and more particularly to a carton for holding insects in the larvae and pupae stages, feeding them, and releasing them when they are in the adult stage.

2. Description of the Prior Art

A prior art search in the U.S. Patent and Trademark Office directed to the subject matter of this application discloses the following patents: U.S. Pat. Nos. 673,285; 2,403,840; 2,814,408; 2,850,224; 3,029,998; 3,115,290; 3,159,328; 3,361,332; 3,375,808; 3,768,723; 4,010,888; 4,368,690; Russian No. 543,374.

None of the prior art patents uncovered in the search disclosed a collapsible insect carton having an internal structure with a pair of upper and lower panels extending between the side and end walls and including means for holding an insect food container.

SUMMARY OF THE INVENTION

An object of the present invention is to provide a collapsible folding carton for hatching and holding insects in the larvae and pupae stages and for releasing them when they reach the adult stage.

A more specific object of the invention is to provide an insect carton having an internal structure adapted to provide insects with a place in which they can hatch, live and feed.

Another specific object of the invention is to provide an insect carton having at least one wall which is readily openable to permit the quick release of insects from the carton.

These and other objects of the invention will be apparent from an examination of the following description and drawings.

It will be understood that, for purposes of clarity, certain elements may have been intentionally omitted from certain views where they are believed to be illustrated to better advantage in other views.

DESCRIPTION OF THE PREFERRED EMBODIMENT

One of the methods commonly employed in fighting insects harmful to humans or agricultural products such as screw worms, Mediterranean Fruit Flies and similar types of insects is to raise and sterilize them and then release then over areas where it is desired to contain and limit the further growth and reproduction of these insects.

The present invention is concerned with a carton adapted to be used in the hatching, holding, feeding, and releasing of insects.

Figure 1:
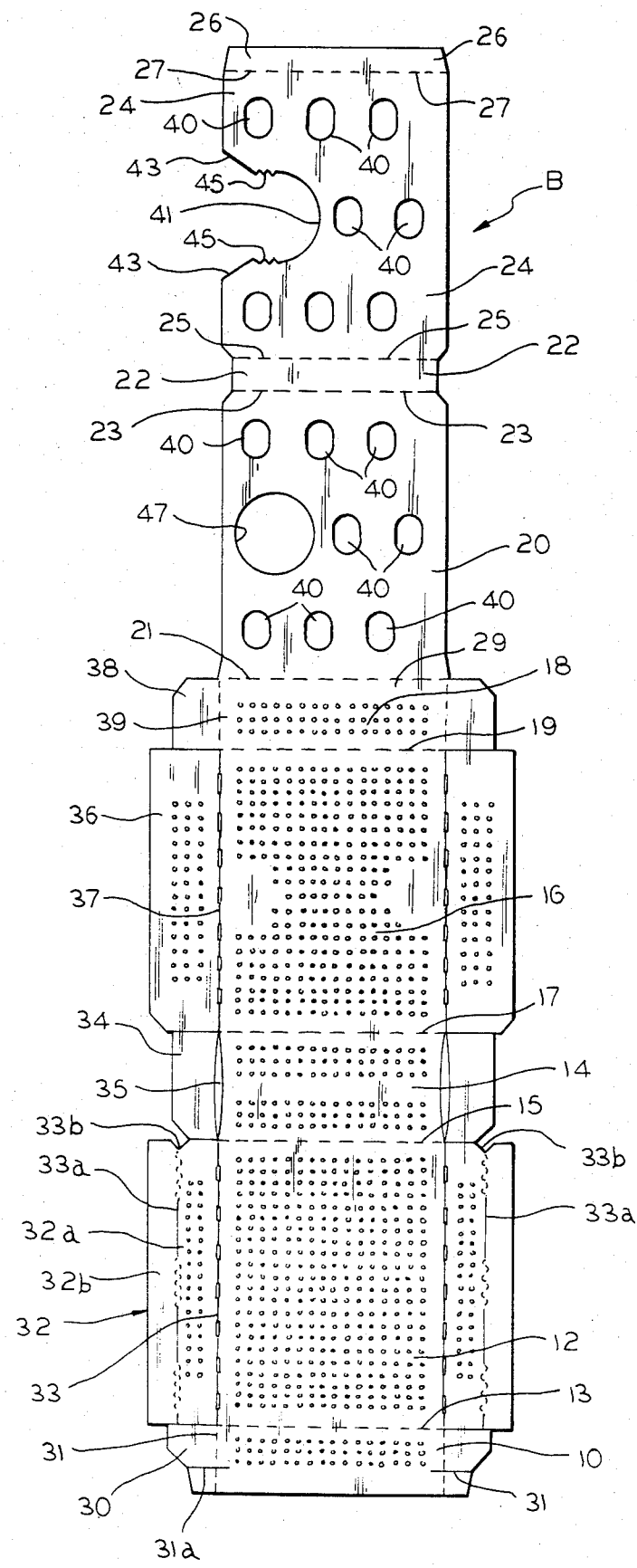
FIG. 1 is a plan of a blank of foldable sheet material from which the carton illustrated in the other views may be formed.
Figure 2:
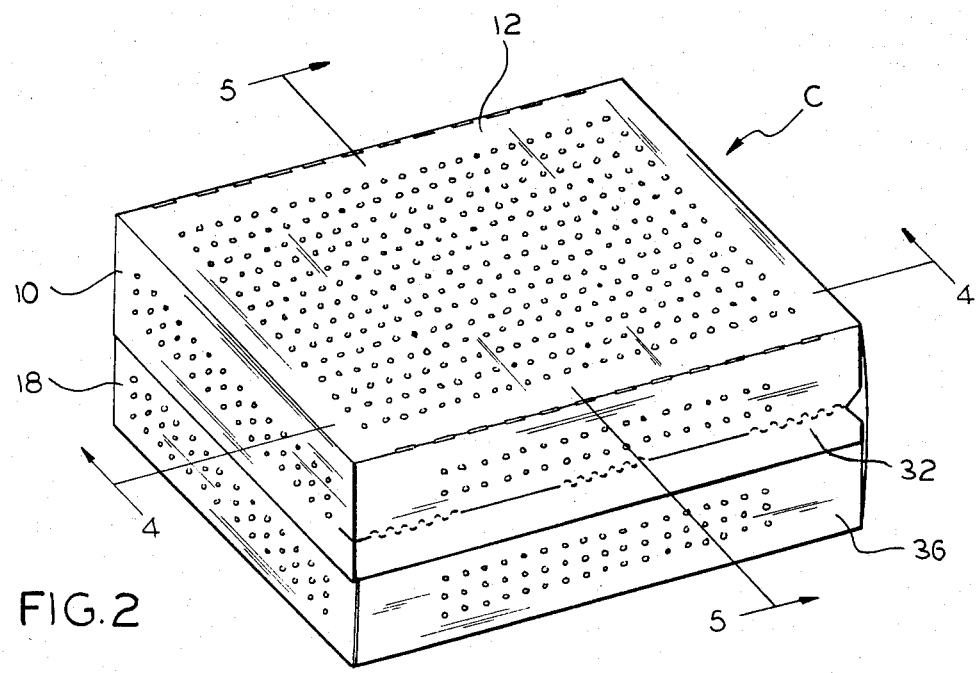
FIG. 2 is a perspective view of a carton embodying features of the invention, which is formed from the structure illustrated in FIG. 1, as shown in a closed position.

Referring now to the drawings for a better understanding of the invention it will be seen that the carton C shown in FIGS. 2-7 may be formed from the unitary blank B of foldable paperboard shown in FIG. 1.

Figure 3:
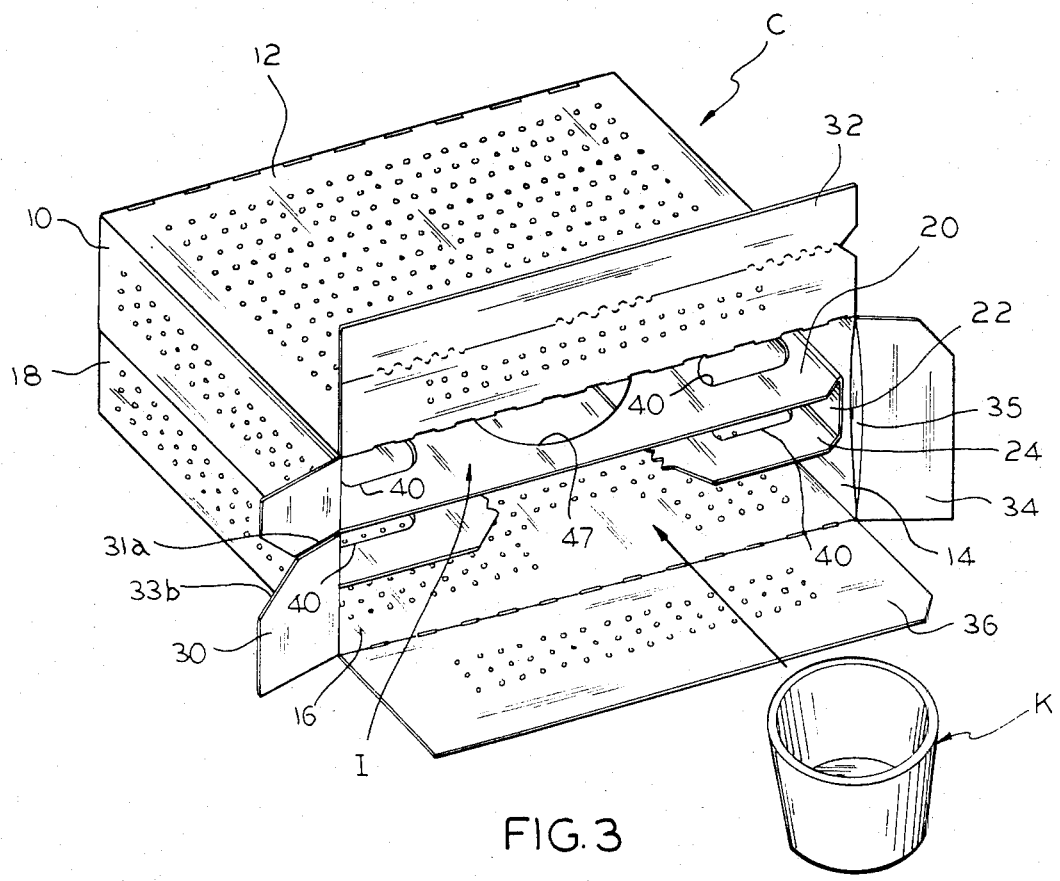
FIG. 3 is a view similar to FIG. 2 but illustrating the carton in an open position.

As best seen in FIGS. 1 and 3, carton C includes a a central or body portion formed from a plurality of panels foldably joined to each other along parallel fold lines in the following manner: first side wall upper panel 10, top wall panel 12, second side wall panel 14, bottom wall panel 16, first side wall lower panel 18, insert upper panel 20, insert first side panel 22, insert lower panel 24, and insert second side panel 26, which are foldably joined to each other along parallel fold lines 13, 15, 17, 19, 21, 23, 25 and 27, respectively.

When the carton is formed first side wall upper and lower panels 10 and 18 are adhesively attached to each other in overlapped relation to form a tubular structure open at the ends, as best seen in FIG. 3. Positioned within the interior of the carton is an integral internal structure or insert I which includes upper and lower panels 20 and 24. These panels are foldably joined to the first and second side flaps 22 and 26, which in turn are adhesively secured to the inner surfaces of the respective carton side wall panels.

It will be noted that the internal structure is spaced upwardly from the carton lower panel 16 and downwardly from the carton upper panel 12, so that a cell is provided on each side of the insert. The ends of the carton may be closed by a plurality of end closure flaps which include: flaps 30, foldably joined on fold lines 31 to opposite ends of first side wall upper panel 10; outer flaps 32, foldably joined on fold lines 33 to opposite ends of top wall panel 12; flaps 34, foldably joined on fold lines 35, to opposite ends of second side wall panel 14; inner flaps 36, foldably joined on fold lines 37 to opposite ends of bottom wall panel 16; and flaps 38, foldably joined on fold lines 39 to opposite ends of first side wall lower panel 18. Fold lines 35 may each be double lines which are bowed away from each other in the manner disclosed in U.S. Pat. No. 3,361,332.

As best seen in FIG. 1, end wall panel outer flaps 32 are each divided into upper and lower sections 32a, and 32b by a weakened line of tear 33a with lower section 32b being adhesively secured to inner flap 36. Also, flaps 32 are provided at corresponding ends with V-shaped notches 33b which are aligned with tear lines 33a. Additionally, flaps 30 are provided with cut lines 31a aligned with tear lines 33a. The purpose of double score lines 35, tear lines 33a, notches 33b, and cut lines 31a is to facilitate rapid opening of the carton by knives in a manner described later herein.

As previously mentioned the internal structure of the carton includes a pair of upper and lower panels 20 and 24, respectively, each of which is provided with a series of openings 40 which permit the insects in the larvae or adult stage to pass back and forth through the various cells of the carton.

Panels 20 and 24 are also provided with larger aligned apertures 47 and 41, respectively, which are adapted to retain in position a cup K which holds food for the insects housed within the carton. Opening 41 may be provided adjacent the edge of the panel 24 with inwardly sloping edges 43 which facilitate entry of the cup into its position, and with jagged sawtooth edges 45, which serve to keep the cup in place after it has once been inserted.

Figure 4:
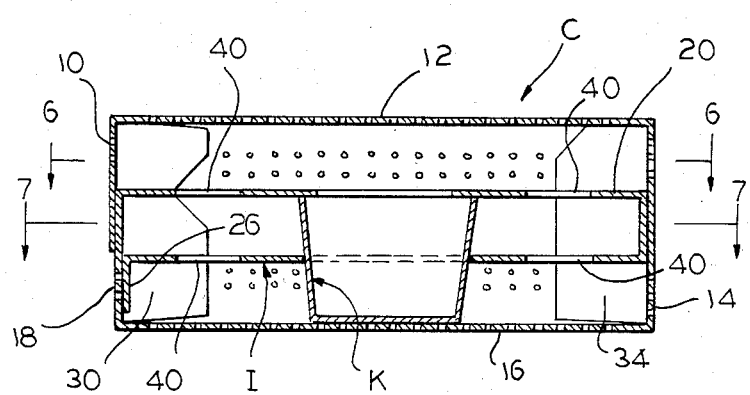
FIGS. 4 and 5 are transverse and longitudinal vertical sectional views taken on lines 4—4 and 5—5, respectively, of the structure illustrated in FIG. 2.
Figure 5:
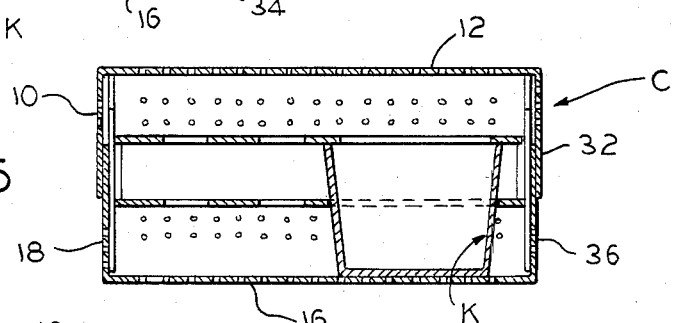
Figure 6:
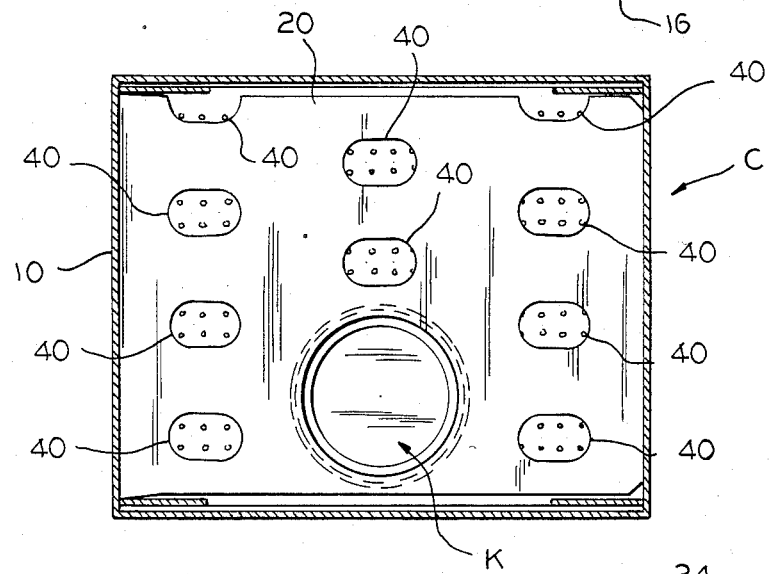
FIGS. 6 and 7 are horizontal sectional views taken on lines 6—6 and 7—7, respectively, of the structure illustrated in FIG. 4.
Figure 7:
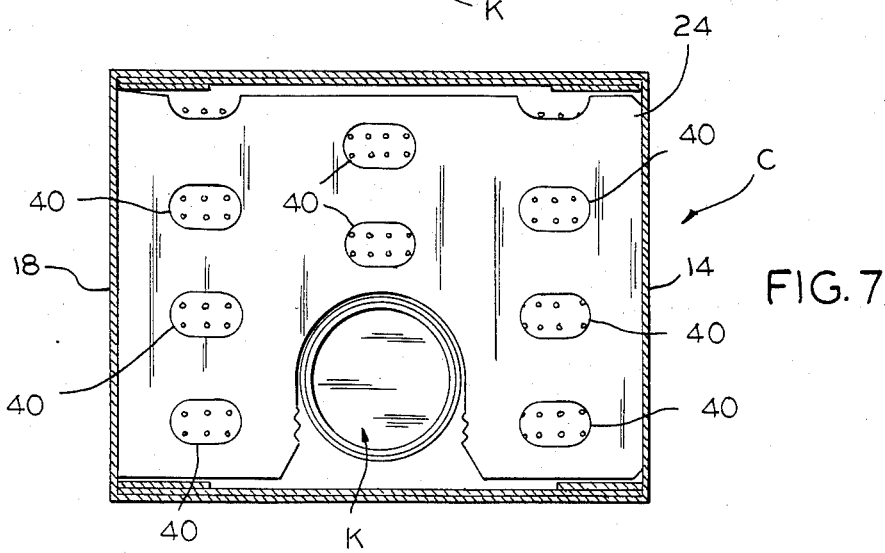

As previously mentioned one of the purposes of the carton is to enable the insects to be released quickly this is accomplished by providing the end walls, as best seen in FIGS. 3 and 4 with perforated lines of separation to permit a knife to be quickly slipped along the end walls to sever them. The dimples provided by bowed scores 35 provide easy access for the knives to notches 33*b*, weakened lines 33*a*, and cut lines 31*a* on each side of the carton. The knives can be positioned on opposite sides of a carton chute so as the cartons are forced out the cartons will be automatically opened as they are ejected into the air from a plane.

What is claimed is:

1. A carton for hatching, holding, feeding, and releasing insects, said carton being formed from a unitary blank of foldable paperboard and comprising:
 (a) pairs of apertured, opposed top and bottom, side, and end wall panels foldably joined to each other to form a vented box-like external structure;
 (b) certain of said end wall panels being readily openable to facilitate quick release of insects from said carton;
 (c) an internal insect holding and feeding structure disposed intermediate said top and bottom wall panels;
 (d) said internal structure including:
  (i) a pair of parallel upper and lower panels spaced vertically from each other and from said top and bottom wall panels and extending between and connected to said side wall panels;
  (ii) said upper and lower panels presenting apertures accommodating the passage of insects therethrough;
  (iii) said upper and lower panels also presenting aligned holes for retaining in place an insect food holding container.

2. A carton according to claim 1, wherein said end walls present weakened lines of tear extending lengthwise thereof and notches at corresponding ends thereof to accommodate access of cutting means to said lines of tear.

* * * * *